United States Patent [19]

Watanabe et al.

[11] 4,370,393
[45] Jan. 25, 1983

[54] SOLID ELECTROLYTES

[75] Inventors: Tetsuo Watanabe, Nagoya; Syunzo Mase, Tobishima; Shigeo Soejima, Nagoya, all of Japan

[73] Assignee: NGK Insulators Ltd., Nagoya, Japan

[21] Appl. No.: 184,979

[22] Filed: Sep. 8, 1980

[30] Foreign Application Priority Data

Sep. 18, 1979 [JP] Japan .................................. 54/118716

[51] Int. Cl.$^3$ .......................... C04B 35/48; H01M 6/18
[52] U.S. Cl. .................................... 429/193; 501/103; 204/195 S
[58] Field of Search .................... 204/195 S; 429/104, 429/193; 106/39.5, 57; 423/266; 501/103

[56] References Cited

U.S. PATENT DOCUMENTS 4,219,359 8/1980 Miwa et al. ...................... 204/195 S
4,266,979 5/1981 Miyoshi et al. ........................ 106/57
4,279,655 7/1981 Garvie et al. ....................... 423/266

Primary Examiner—Mark Bell
Attorney, Agent, or Firm—Stevens, Davis, Miller & Mosher

[57] ABSTRACT $ZrO_2$-$Y_2O_3$ solid electrolytes having a high strength and an excellent deterioration property so as to be durable for a long time, comprised mainly of cubic crystal and monoclinic crystal or cubic crystal, monoclinic crystal and tetragonal crystal, wherein an average grain size of monoclinic crystal or tetragonal crystal is not greater than 2 μm and a ratio of the intensity of the monoclinic (III) X-ray diffraction line to that of the cubic (200) line is 0.01–2.5. In the case of solid electrolytes comprised mainly of cubic crystal, monoclinic crystal and tetragonal crystal, the following definition is necessary. A ratio of the intensity of the tetragonal (200) X-ray diffraction line to that of the cubic (200) line is not greater than 1.0.

1 Claim, 11 Drawing Figures (5000 Magnifications)

(5000 Magnifications)

(5000 Magnifications)

(5000 Magnifications)

(5000 Magnifications)

(10000 Magnifications)

SOLID ELECTROLYTES

The present invention relates to oxygen ion conductive $ZrO_2$-$Y_2O_3$ solid electrolytes most suitable for use in a device for measuring oxygen concentration in which the strength and the deterioration of the electrolytes resulting from the lapse of time due to use for a long time have been improved.

Solid electrolytes consisting of stabilized zirconia ceramics containing about 8–10 mol% of $Y_2O_3$ have been heretofore broadly used as oxygen ion conductive solid electrolytes. However, the solid electrolytes consisting of such stabilized zirconia ceramics are stable at a temperature range from room temperature to about 1,000° C. and do not substantially cause the deterioration with lapse of time, but they are low in the strength, so that when such solid electrolytes are used for, for example, as an oxygen sensor for measuring oxygen concentration in automotive exhaust gas, these electrolytes are very readily broken by thermal shock.

Furthermore, solid electrolytes having improved strength and thermal shock resistance consisting of so-called partially stabilized zirconia ceramics containing less than 7 mol% of $Y_2O_3$ have been known. However, it has been found that the prior solid electrolytes consisting of $Y_2O_3$ partially stabilized zirconia ceramics have major defects such as great deterioration with lapse of time at a temperature range of 200° C.–300° C., a large number of fine cracks are formed at the solid electrolyte surface, water is absorbed, and the strength is noticeably deteriorated and the electrolytes are broken when said electrolytes are used at said temperature for a long time.

The present invention intends to obviate the defects of the prior solid electrolytes consisting of the stabilized zirconia ceramics while providing excellent strength and thermal shock resistance as well as improving the deterioration of strength at a temperature range of 200° C.–300° C. with lapse of time, this being the defect of the prior solid electrolytes consisting of the partially stabilized zirconia ceramics. The present invention consists in solid electrolytes of zirconia ceramics which consist mainly of cubic crystal and monoclinic crystal owing to addition of $Y_2O_3$, in which an average grain size of the monoclinic crystal is not greater than 2 $\mu$m and a ratio of the intensity of the monoclinic $(11\bar{1})$ X-ray diffraction line to that of the cubic (200) line is 0.01–2.5, as well as with solid electrolytes of zirconia ceramics which consist mainly of cubic crystal, monoclinic crystal and tetragonal crystal owing to addition of $Y_2O_3$ and in which an average grain size of the monoclinic crystal and the tetragonal crystal is not greater than 2 $\mu$m and a ratio of the intensity of the monoclinic $(11\bar{1})$ X-ray diffraction line to that of the cubic (200) line is 0.01–2.5 and a ratio of the intensity of the tetragonal (200) X-ray diffraction line to that of the cubic (200) line is not greater than 1.0.

Thus, the inventors have found that in order to improve the strength, the thermal shock resistance, and the deterioration of strength at a temperature range of 200° C.–300° C. with lapse of time, it is very important that the grain size of the monoclinic crystal and the tetragonal crystal is smaller than the particularly defined value while the X-ray diffraction line intensity ratio of the particularly defined planes of the monoclinic crystal and the cubic crystal and the X-ray diffraction line intensity ratio of the particularly defined planes of the tetragonal crystal and the cubic crystal are within the ranges of the particularly defined numerical values.

In other words, the present invention is based on the discovery that the solid electrolytes consisting of the prior $Y_2O_3$ partially stabilized zirconia ceramics deteriorate the strength with lapse of time in a very short time when used at a temperature range of 200° C.–300° C. as mentioned above, and has clarified the cause of the deterioration.

That is, in the solid electrolytes consisting of the partially stabilized zirconia ceramics owing to addition of $Y_2O_3$, the cubic crystal and the tetragonal crystal are the stable phase at the sintering temperature range (usually 1,600°–1,800° C.) but the cubic crystal and the monoclinic crystal are the stable phase at room temperature, so that at the cooling course from a high temperature zone to room temperature, practically at a temperature of about 400° C., the crystal is transformed from the tetragonal crystal to the monoclinic crystal, and when all the tetragonal crystal is transformed into the monoclinic crystal, the solid electrolyte consists of the cubic crystal and the monoclinic crystal and when a part of the tetragonal crystal remains, the solid electrolyte consists of the cubic crystal, the monoclinic crystal and the tetragonal crystal. When the tetragonal crystal is transformed into the monoclinic crystal, the volume of the grains expands. However, in the prior solid electrolytes composed of $Y_2O_3$ partially stabilized zirconia ceramics consisting of the cubic crystal and the monoclinic crystal or the cubic crystal, the monoclinic crystal and the tetragonal crystal, the average grain size of the monoclinic crystal and the tetragonal crystal is as large or greater than 3 $\mu$m, so that the volume expansion per each grain due to the crystal transformation is large and strain is locally applied to the interface between the grains of monoclinic crystal and the cubic crystal with the result being an excess stress which exists at the grain boundary, and the local stress is increased by exposing the solid electrolyte to a temperature range of 200° C.–300° C. for a long time, and fine cracks are formed presumably resulting in the breakage. The mechanism of deterioration with lapse of time is the inherent phenomenon of $Y_2O_3$ partially stabilized zirconia ceramics in which the transformation temperature from the tetragonal crystal to the monoclinic crystal is low. FIG. 1 shows the relation between the grain size of the monoclinic or the tetragonal crystal and the flexural strength of $Y_2O_3$ stabilized zirconia ceramics, wherein curve $a_1$ indicates flexural strength of new specimens, while curve $b_1$ indicates flexural strength of specimens after heating and cooling between 200° C. and 300° C. for 1,000 hours. Thus, as shown in FIG. 1, the deterioration with lapse of time is considerably increased with an increase of the grain size of the monoclinic crystal or the tetragonal crystal, and when the grain size is greater than 2 $\mu$m, the deterioration with lapse of time becomes suddenly noticeable. Accordingly, it has been found that the prior solid electrolytes, wherein the grain size of the monoclinic crystal or the tetragonal crystal is greater than 3 $\mu$m, have a large deterioration with lapse of time and the grain size has a high relation to the deterioration with lapse of time. In addition, the content ratio of the monoclinic crystal and the tetragonal crystal highly influences the deterioration with lapse of time. That is, the relation of the deterioration with lapse of time to each intensity ratio ($M_{(11\bar{1})}/C_{(200)}$ or $T_{(200)}/C_{(200)}$) of X-ray diffraction line, where ($M_{(11\bar{1})}$) is the intensity of (11$\bar{1}$) plane of the monoclinic crystal X-ray diffraction line, $T_{(200)}$ is the intensity of (200) plane of the tetragonal crystal X-ray diffraction line and $C_{(200)}$ is the intensity of (200) plane of the cubic crystal X-ray diffraction line, is as shown in FIG. 2 and FIG. 3, and when $M_{(11\bar{1})}/C_{(200)}$ exceeds 2.5 or $T_{(200)}/C_{(200)}$ exceeds 1.0, the deterioration with lapse of time is suddenly increased. Herein, curves $a_2$ and $a_3$ indicate flexural strength of new specimens, and curves $b_2$ and $b_3$ indicate flexural strength of specimens after heating and cooling between 200° C. and 300° C. for 1,000 hours in FIGS. 2 and 3. This reason presumably relates to the above mentioned crystal transformation. Based on these discovered results, the optimum grain size of the monoclinic crystal and the tetragonal crystal and the optimum values of X-ray diffraction line intensity ratio at the particularly defined planes of the monoclinic crystal, the tetragonal crystal and the cubic crystal have been determined.

For estimation of the monoclinic crystal and the tetragonal crystal, the intensity of X-ray diffraction line at the as fired surface or mirror polished surface of the ceramics was used. The intensity of X-ray diffraction line was indicated by the height from the background measured at room temperature under condition of $2\theta = 1°$/min. of rotation rate of goniometer, time constant of 0.5 second, slit system of 1°-1°-0.15 mm with Ni filter and using CuK$\alpha$ ray in which X-ray tube voltage is 50 kv and X-ray tube current is 80 mA. In this case, the X-ray diffraction line intensity of (11$\bar{1}$) plane of the monoclinic crystal is height $h_1$ wherein the plane portion at both sides of the diffraction line is the background as shown in FIG. 4. The X-ray diffraction line intensity of (200) plane of the cubic crystal, when there is no tetragonal crystal, is the same as in the measurement of FIG. 4, and when the tetragonal crystal is present, is height $h_2$ wherein the plane level at both sides of X-ray diffraction line group is the background as shown in FIG. 5.

The X-ray diffraction line intensity of (200) plane of the tetragonal crystal is height $h_3$ wherein the tangent crossing the foots at both sides of the diffraction line is the background as shown in FIG. 6. The average crystal grain size of the monoclinic crystal or the tetragonal crystal is an average of value obtained by multiplying a diameter corresponding to a circle in the cross-section of zirconia ceramics by $\sqrt{3/2}$ (correction coefficient in order that the maximum diameter portion of the crystal grain at the cross-section is not cut) and as a process for identifying the crystal phase of the monoclinic crystal and the tetragonal crystal, these crystals are classified by measuring count number of yttrium K$\alpha$ of individual crystal grain by means of EPMA (electron probe microanalyzer). The term "count number of yttrium K$\alpha$" used herein means a value obtained by subtracting the count number of background from the found count number and this value is substantially proportional to the content of yttrium. That is, the crystal grain in which the count number of yttrium K$\alpha$ is relatively large, is cubic crystal and the crystal grain in which the count number of yttrium K$\alpha$ is less than 0.7 time of the count number of yttrium K$\alpha$ of the cubic crystal is the monoclinic crystal or the tetragonal crystal.

An explanation will be made with respect to the reason of the limitation of the numerical values of the present invention.

When the average grain size of the monoclinic crystal or the tetragonal crystal exceeds 2 $\mu$m, even if the total amount of the monoclinic crystal or the tetragonal crystal is slight, an excess stress is locally caused in the ceramics and zirconia ceramics having a low deterioration with lapse of time is not obtained as mentioned above, so that the grain size is preferred to be not greater than 1.6 $\mu$m. Furthermore, when the amount of the monoclinic crystal is more than 2.5 in the ratio of the intensity of the monoclinic (11$\bar{1}$) X-ray diffraction line to that of the cubic (200) line, the stress owing to the crystal transformation from the tetragonal crystal to the monoclinic crystal is excessive and zirconia ceramics having a high flexural strength and a low deterioration with lapse of time cannot be obtained. The preferable ratio of the intensity is not greater than 2. When said ratio is less than 0.01, the satisfactory strength cannot be obtained, so that said ratio is preferred to be not less than 0.01, more preferably not less than 1. When the ratio of the intensity of the tetragonal (200) X-ray diffraction line to that of the cubic (200) line exceeds 1.0, the decrease of the strength and the crack formation of zirconia ceramics are caused due to the crystal transformation and the thermal expansion difference, so that such a ratio is not preferable.

The term "ZrO$_2$ ceramics obtained by addition of Y$_2$O$_3$" used in the present invention means zirconia ceramics obtained mainly by using Y$_2$O$_3$ as a stabilizer for ZrO$_2$ and of course includes ones wherein about not more than 30 mol% of Y$_2$O$_3$ is substituted with oxides of other rare earth elements, for example, Yb$_2$O$_3$, Sc$_2$O$_3$, Nd$_2$O$_3$, Gd$_2$O$_3$, Sm$_2$O$_3$ and the like, or CaO, MgO, or ones containing not more than 10% by weight of aluminum oxide, silicon dioxide and the like, or mixtures or compounds thereof, for example, clay, kaolin, mullite and the like, in addition to zirconium oxide.

Solid electrolytes according to the present invention can be obtained, for example, by the following processes. To ZrO$_2$ powder consisting mainly of monoclinic crystal and having a specific surface area of 3–15 m$^2$/g measured by BET method is added and homogeneously dispersed and mixed Y$_2$O$_3$ powder which is finer than ZrO$_2$ powder, in a molar ratio of Y$_2$O$_3$/ZrO$_2$ being 4/96–7/93. For the purpose, a solution of yttrium compound, for example, an aqueous solution of YCl$_3$ or Y(NO$_3$)$_3$ is mixed with ZrO$_2$ and the mixture is dried and thermally decomposed. Alternatively, Y$_2$O$_3$ fine powder and ZrO$_2$ fine powder are thoroughly mixed by ball mill and the like. Then, 0.5–5% by weight of Al$_2$O$_3$ or clay powder is added and mixed thereto as a sintering aid, and resulted with a mixture having a specific surface area of 5–20 m$^2$/g. The thus formed mixture is shaped into a desired form by well known process, for example, press molding, and sintered at a temperature of 1,400° C.–1,500° C. to obtain solid electrolyte according to the present invention.

In the above described production process, the specific surface area of the mixture and the firing temperature are particularly important for obtaining the solid electrolytes according to the present invention. That is, when the specific surface area of the mixture is too small, the firing temperature must be higher for obtaining the sintered body, and this is liable to make the grain size of the monoclinic crystal or the tetragonal crystal too large. When the specific surface area of the mixture is too large, even if the firing is effected at the above described temperature range, the grain size of the monoclinic crystal or the tetragonal crystal is liable to become too large.

Even by using production conditions other than of the above described scope, the solid electrolytes according to the present invention can be obtained, but in such a case, the selection of the starting materials and the adjustment of various conditions are necessary.

The present invention will be explained in more detail.

For better understanding of the invention, reference is taken to the accompanying drawings, wherein.

Figure 1:
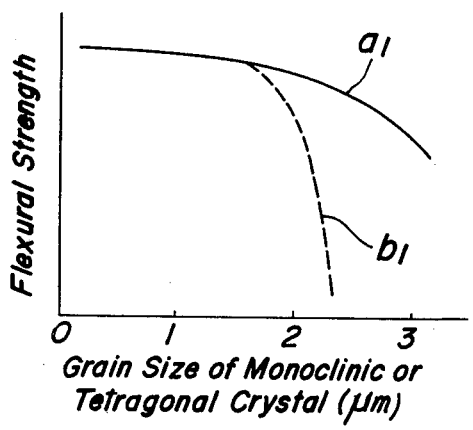
FIG. 1 is a graph showing the relation of the grain size of the monoclinic crystal or the tetragonal crystal to the flexural strength.
Figure 2:
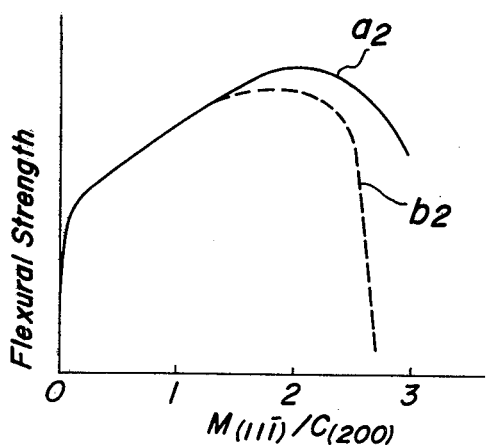
FIGS. 2 and 3 show graphs showing the relation of the ratio of the intensity of X-ray diffraction line to the flexural strength.
Figure 3:
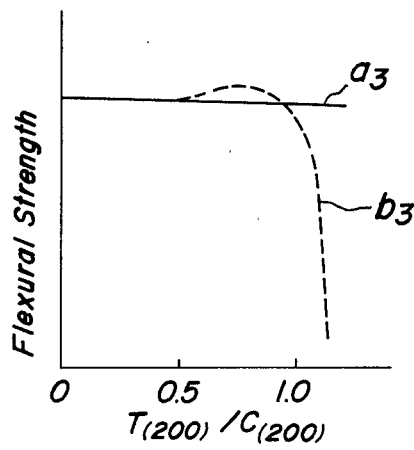
Figure 4:
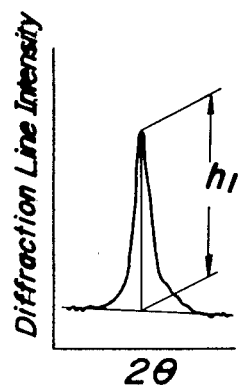
FIGS. 4 to 6 are schematic views for explaining the method for measuring X-ray diffraction line intensity of the monoclinic crystal, the cubic crystal and the tetragonal crystal.
Figure 5:
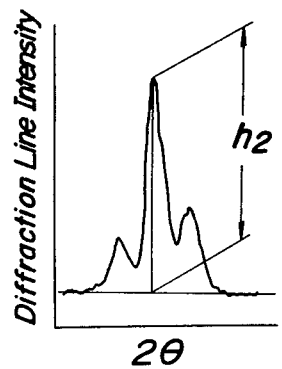
Figure 6:
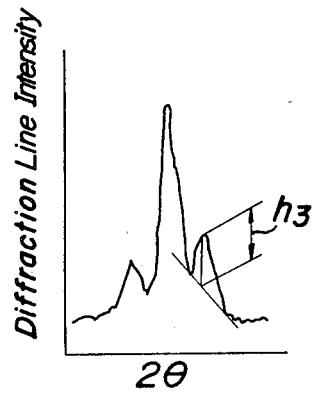
Figure 7:
FIG. 7 is a microphotograph (5,000 magnifications) of the prior partially stabilized zirconia ceramics obtained by addition of yttrium.
Figure 8:
Figure 9:
Figure 10:
Figure 11:

FIG. 8 is a microphotograph (5,000 magnifications) of the zirconia ceramics in FIG. 7 after the heating and cooling cycle between 200° C. and 300° C. for 100 hours;

FIG. 9 is a microphotograph (5,000 magnifications) of a solid electrolyte of the present invention;

FIG. 10 is a microphotograph (5,000 magnifications) of the solid electrolyte in FIG. 9 after the heating and cooling cycle between 200° C. and 300° C. for 1,500 hours; and FIG. 11 is a microphotograph (10,000 magnifications) explaining the grain size of the monoclinic crystal or the tetragonal crystal of the portion A in FIG. 9.

The following examples are given for the purpose of illustration of this invention and are not intended as limitations thereof.

EXAMPLE 1

To monoclinic crystal $ZrO_2$ powder having a specific surface area of 6 $m^2/g$ measured by BET method was added an aqueous solution of $YCl_3$ in a molar ratio of $Y_2O_3/ZrO_2$ being 5/95, the mixture was dried, then $YCl_3$ was thermally decomposed at 1,000° C., and 3% by weight of clay powder having a specific surface area of 25 $m^2/g$ was added thereto and mixed by ball mill to obtain the powdery mixture of a specific surface area of 17 $m^2/g$. This powdery mixture was pressed under a pressure of 1 ton/$cm^2$ by press molding to obtain a shaped article and the shaped article was fired at 1,500° C. for 1 hour to obtain a zirconia solid electrolyte having an apparent density of 5.85 g/$cm^3$, an average grain size of the monoclinic crystal and the tetragonal crystal of 0.9 μm, crystal phase $M_{(11\bar{1})}/C_{(200)}=1.2$, $T_{(200)}/C_{(200)}=0.1$.

EXAMPLE 2

$ZrO_2$ and $Y_2O_3$ or the compounds thereof were prepared and mixed in a ball mill so as to obtain the composition shown in Table 1. The mixture was calcined at 1,000° C. and pulverized in a ball mill by wet method and then dried. The obtained powder was press molded into 0.5 cm × 0.5 cm × 6 cm and the moldings were fired at a temperature of 1,350° C.–1,530° C. for 1–3 hours to obtain solid electrolytes composed of zirconia ceramics according to the present invention. The obtained solid electrolytes were measured with respect to the intensity ratio of X-ray diffraction line, the crystal grain size of the monoclinic crystal or the tetragonal crystal, the flexural strength, the thermal shock resistance, and the flexural strength and the thermal shock resistance after repeating the heating and cooling between 200° C. and 300° C. at a heating and cooling temperature rate of 10° C./min. for 1,500 hours in an electric furnace. The obtained results are shown in Table 1. Table 1 discloses those which are beyond the limitation scope of numerical values of the present invention as Comparative Examples. Anyone of the solid electrolytes in Examples in the present invention was satisfactorily low as 500–2,000 Ω.cm in volume resistivity at 600° C. The solid electrolytes according to the present invention did not substantially show the water absorption at the ceramics surface in the coloration test using a dyestuff even after the heat cycle of 1,500 hours between 200° C. and 300° C.

Microphotographs of Sample No. 10 and No. 22 before and after the heat cycle are shown in FIG. 7 to FIG. 11.

TABLE 1(a)

| | No. | Molar ratio of stabilizer to $ZrO_2$ | Composition of stabilizer | Average grain size of monoclinic or tetragonal crystal (μm) | $M_{(11\bar{1})}/C_{(200)}$ | $T_{(200)}/C_{(200)}$ | Flexural strength (kg/$cm^2$) | Thermal shock resistance (°C./sec) | Flexural strength after heating at 200° C.–300° C. for 1,500 hours (kg/$cm^2$)* | Thermal shock resistance after heating at 200° C.–300° C. for 1,500 hours (°C./sec)* |
|---|---|---|---|---|---|---|---|---|---|---|
| Present | 1 | 6/94 | $Y_2O_3$ | 0.2 | 0.4 | 0 | 3,300 | 40 | 3,300 | 40 |
| inven- | 2 | 7/93 | $Y_2O_3$ | 0.3 | 0.01 | 0 | 2,500 | 30 | 2,600 | 30 |
| tion | 3 | 5.5/94.5 | $Y_2O_3$ | 0.3 | 1.1 | 0 | 4,100 | 45 | 4,000 | 45 |
| | 4 | 4.8/95.2 | $Y_2O_3$ | 0.5 | 1.9 | 0 | 5,000 | 60 | 4,100 | 45 |
| | 5 | 3.5/96.5 | $Y_2O_3$ | 0.6 | 2.4 | 0 | 4,400 | 50 | 3,000 | 30 |
| | 6 | 5/95 | $Y_2O_3$ | 1.0 | 0.05 | 0 | 2,600 | 30 | 2,600 | 30 |
| | 7 | 4.5/95.5 | $Y_2O_3$ | 2.0 | 1.5 | 0 | 3,500 | 45 | 2,600 | 30 |
| | 8 | 6/94 | $Y_2O_3$ | 0.2 | 1.2 | 0.5 | 4,200 | 45 | 4,200 | 45 |
| | 9 | 4/96 | $Y_2O_3$ | 0.3 | 1.7 | 0.2 | 5,000 | 60 | 4,300 | 50 |
| | 10 | 6.5/93.5 | $Y_2O_3$ | 0.4 | 0.6 | 0.4 | 3,500 | 40 | 3,500 | 40 |

TABLE 1(b)

|  | No. | Molar ratio of stabilizer to $ZrO_2$ | Composition of stabilizer | | Average grain size of monoclinic or tetragonal crystal (μm) | $M_{(11\bar{1})}/C_{(200)}$ | $T_{(200)}/C_{(200)}$ | Flexural strength (kg/cm²) | Thermal shock resistance (°C./sec) | Flexural strength after heating at 200° C.-300° C. for 1,500 hours (kg/cm²)* | Thermal shock resistance after heating at 200° C.-300° C. for 1,500 hours (°C./sec)* |
| --- | --- | --- | --- | --- | --- | --- | --- | --- | --- | --- | --- |
| Present invention | 11 | 5.5/94.5 | $Y_2O_3$ | | 0.8 | 0.3 | 0.8 | 3,000 | 30 | 3,700 | 40 |
| | 12 | 6/94 | $Y_2O_3$ | | 1.2 | 0.04 | 0.9 | 2,600 | 30 | 2,900 | 30 |
| | 13 | 5/95 | $Y_2O_3$ | | 1.9 | 1.1 | 0.7 | 3,200 | 40 | 2,400 | 30 |
| | 14 | 6/94 | $Y_2O_3$ $Yb_2O_3$ | 70 mol % 30 mol % | 0.5 | 1.3 | 0.5 | 4,500 | 50 | 4,400 | 50 |
| | 15 | 5.5/94.5 | $Y_2O_3$ CaO | 70 mol % 30 mol % | 0.9 | 1.2 | 0 | 4,000 | 45 | 4,000 | 45 |
| Comparative Example | 16 | 8/92 | $Y_2O_3$ | | — | 0 | 0 | 1,000 | 20 | 1,000 | 20 |
| | 17 | 7/93 | $Y_2O_3$ | | 0.3 | 0.005 | 0 | 1,400 | 20 | 1,400 | 20 |
| | 18 | 5/95 | $Y_2O_3$ | | 0.4 | 2.8 | 0 | 1,700 | 65 | <100 | <10 |

TABLE 1(c)

| | No. | Molar ratio of stabilizer to $ZrO_2$ | Composition of stabilizer | Average grain size of monoclinic or tetragonal crystal (μm) | $M_{(11\bar{1})}/C_{(200)}$ | $T_{(200)}/C_{(200)}$ | Flexural strength (kg/cm²) | Thermal shock resistance (°C./sec) | Flexural strength after heating at 200° C.-300° C. for 1,500 hours (kg/cm²)* | Thermal shock resistance after heating at 200° C.-300° C. for 1,500 hours (°C./sec)* |
| --- | --- | --- | --- | --- | --- | --- | --- | --- | --- | --- |
| Comparative Example | 19 | 6.7/93.3 | $Y_2O_3$ | 2.4 | 0.1 | 0 | 2,100 | 40 | 600 | 10 |
| | 20 | 4/96 | $Y_2O_3$ | 1.4 | 2.7 | 0.5 | 2,200 | 70 | <100 | <10 |
| | 21 | 5.8/94.2 | $Y_2O_3$ | 1.1 | 0.8 | 1.2 | 3,500 | 40 | <100 | <10 |
| Prior sample | 22 | 5/95 | $Y_2O_3$ | 3.0 | 0.9 | 0.3 | 2,700 | 40 | <100 | <10 |

Note:
$M_{(11\bar{1})}$: X-ray diffraction line intensity of $(11\bar{1})$ plane of monoclinic crystal
$T_{(200)}$: X-ray diffraction line intensity of (200) plane of tetragonal crystal
$C_{(200)}$: X-ray diffraction line intensity of (200) plane of cubic crystal
*200° C.-300° C.: Heating and cooling cycle between 200° C. and 300° C.

As seen from the data of Table 1, the solid electrolytes of the present invention are high in strength and excellent in thermal shock resistance. They also have small variations with lapse of time even after having been used for a long time, and they are satisfactorily low in volume resistivity.

As shown in FIG. 7, in the solid electrolyte of sample No. 22 composed of prior $ZrO_2$-$Y_2O_3$ partially stabilized zirconia ceramics, the average grain size of the monoclinic crystal and tetragonal crystal (both: M) present between the cubic crystal grains (C) is about 3 μm and fine cracks (D) are formed in the ceramics as shown in FIG. 8 after the heat cycle of 100 hours. After 300 hours, the solid electrolyte was broken, while in the solid electrolyte of sample No. 10 of the present invention, the grain size of the monoclinic crystal and the tetragonal crystal is not larger than 2 μm (average grain size: 0.4 μm), as shown in FIG. 9, and after the heat cycle of 1,500 hours, no cracks were formed as shown in FIG. 10 and in the above described coloration test using a dyestuff, the penetration of the dyestuff not being found. In FIG. 9, a circle marked portion A is a monoclinic crystal or a tetragonal crystal from the count number of yttrium Kα and the grain size of FIG. 9 seems to be larger, but if this portion is subjected to etching treatment, it is apparent, as shown in FIG. 11, that this portion is an assemble of fine particles and the particle size of these particles is the grain size of the monoclinic crystal or the tetragonal crystal.

As mentioned above, the solid electrolytes of the present invention, in which the grain size of the monoclinic crystal and the tetragonal crystal is very fine (not greater than 2 μm) and the ratio of X-ray diffraction line intensity of the particularly defined planes of the monoclinic crystal and the cubic crystal is within the particularly defined numerical value range, can noticeably improve the strength, the thermal shock resistance, and the deterioration of strength with lapse of time at a temperature range from 200° C. to 300° C. Further, these solid electrolytes can be used as oxygen ion conductive solid electrolytes for a device for measuring oxygen concentration directly inserted into internal combustion engines, combustion furnaces and the like, or flame detecting devices directly inserted into flame, and these solid electrolytes are very commercially useful.

What is claimed is:

1. A solid electrolyte of $ZrO_2$ ceramics consisting essentially of cubic crystals, monoclinic crystals and tetragonal crystals owing to addition of $Y_2O_3$, having an average grain size of monoclinic crystals and tetragonal crystals of not greater than 2 μm, a ratio of the intensity of the monoclinic $(11\bar{1})$ X-ray diffraction line to that of the cubic (200) line being 0.01–2.5 and a ratio of the intensity of the tetragonal (200) X-ray diffraction line to that of the cubic (200) line being not greater than 1.0, wherein monoclinic crystal grains and tetragonal crystal grains are present between cubic crystal grains.

* * * * *